(12) United States Patent
Cachemaille et al.

(10) Patent No.: US 8,999,177 B2
(45) Date of Patent: Apr. 7, 2015

(54) OUT-OF PLANE MICRONEEDLE MANUFACTURING PROCESS

(75) Inventors: Astrid Cachemaille, Lausanne (CH); Francois Cannehan, Lausanne (CH)

(73) Assignee: Debiotech S.A., Lausanne (CH)

( * ) Notice: Subject to any disclaimer, the term of this patent is extended or adjusted under 35 U.S.C. 154(b) by 99 days.

(21) Appl. No.: 12/808,334

(22) PCT Filed: Oct. 17, 2008

(86) PCT No.: PCT/IB2008/054280
§ 371 (c)(1),
(2), (4) Date: Jul. 13, 2010

(87) PCT Pub. No.: WO2009/077892
PCT Pub. Date: Jun. 25, 2009

(65) Prior Publication Data
US 2010/0280458 A1    Nov. 4, 2010

(30) Foreign Application Priority Data

Dec. 17, 2007 (EP) .................................... 07123416

(51) Int. Cl.
C25F 3/00 (2006.01)
B44C 1/22 (2006.01)
C03C 15/00 (2006.01)
B81C 1/00 (2006.01)
A61M 37/00 (2006.01)

(52) U.S. Cl.
CPC ........ *B81C 1/00111* (2013.01); *A61M 37/0015* (2013.01); *A61M 2037/0053* (2013.01); *B81B 2201/055* (2013.01)

(58) Field of Classification Search
USPC ........ 216/11, 58, 67; 438/707, 710, 713, 714, 438/719, 734, 749, 750
See application file for complete search history.

(56) References Cited

U.S. PATENT DOCUMENTS 5,683,546 A * 11/1997 Manaka ............................ 216/2
2004/0267205 A1 * 12/2004 Stemme et al. ................ 604/173
2008/0157427 A1 * 7/2008 Chiou et al. .................. 264/220

FOREIGN PATENT DOCUMENTS

| EP | 0 597 302 | 5/1994 |
|----|-----------|--------|
| EP | 0597302 | 5/1994 |
| EP | 1 669 100 | 6/2006 |
| JP | 6-140641 | 5/1994 |

(Continued)

OTHER PUBLICATIONS

Roxhed, N et al. "Penetration-enhanced ultrasharp microneedles and prediction on skin interaction for efficient transdermal drug delivery" J. Microelectromech. Sys. Dec. 6, 2007 vol. 16 No. 6 p. 1429-1440.*

Griss, P et al. "Side-opened out-of-phane microneedles for microfluidic transdermal liquid transfer" J. Microelectromech. Sys. Jun. 25, 2003 vol. 12 No. 3 p. 296-301.*

International Search Report for PCT/IB2008/054280, mailed May 13, 2009.

Written Opinion of the International Searching Authority for PCT/IB2008/054280, mailed May 13, 2009.

(Continued)

*Primary Examiner* — Allan Olsen
*Assistant Examiner* — Margaret D Klunk
(74) *Attorney, Agent, or Firm* — Nixon & Vanderhye, PC

(57) ABSTRACT

Out-of-plane microneedle manufacturing process comprising the simultaneous creation of a network of microneedles and the creation of a polygonal shaped hat (2) above each microneedle (1) under formation, said process comprising the following steps: providing bridges (3) between the hats (3), maintaining the bridges (3) during the remaining microneedle manufacturing steps, removing the bridges (3), together with the hats (2), when the microneedles (1) are formed.

4 Claims, 11 Drawing Sheets

(56) References Cited

FOREIGN PATENT DOCUMENTS

| | | |
|---|---|---|
| JP | 2004-538106 | 12/2004 |
| JP | 2005-199392 | 7/2005 |
| WO | 03/015860 | 2/2003 |
| WO | WO 03/015860 A1 | 2/2003 |
| WO | 2008/003564 | 1/2008 |

OTHER PUBLICATIONS

Lang W: "Silicon Microstructuring Technology", Materials Science and Engineering R: Reports, Elsevier Sequoia S.A., Lausanne, CH, vol. 17, No. 1, Sep. 1, 1996, pp. 1-55, XP004013096.

Japanese Office Action dated Dec. 18, 2012 and its English translation.

\* cited by examiner

FIGURE 2 (AA')

OUT-OF PLANE MICRONEEDLE MANUFACTURING PROCESS

This application is the U.S. national phase of International Application No. PCT/IB2008/054280, filed 17 Oct. 2008, which designated the U.S. and claims priority to European Application No. 07123416.5, filed 17 Dec. 2007, the entire contents of each of which are hereby incorporated by reference.

FIELD OF INVENTION

The present invention relates to microneedles which are manufactured from a wafer, for instance a silicon wafer. The microneedles according to the invention may advantageously be used in the medical field, for intradermally administering a fluid in the body.

STATE OF THE ART

MEMS Microneedles may be classified in two groups, namely in-plane microneedles and out-of-plane microneedles. In the first group the microneedle shaft is parallel to the wafer while in the second group the shaft is perpendicular to the substrate. The out-of-plane microneedle group may itself be divided in two sub-groups, i.e. hollow microneedles and solid microneedles. The hollow microneedles have a through hole as described e.g. in patent applications WO 2002/017985 WO0217985 and WO 2003/015860. The microneedle manufacturing processes disclosed in the prior art use different designs and a combination of photolithography and etching (dry and/or wet etching) to obtain different microneedle shapes. A common feature in all those processes is the presence of a protective mask, generally made of silicon dioxide, above each microneedle under formation. This mask is commonly named "hat".

Some problems are however observed with the state-of-the-art microneedle manufacturing processes. For instance, in the manufacture of out-of-plane microneedles, the yield is limited by the difference of silicon etch rate between the centre and the border of the wafer. Because of this difference some microneedle hats (generally at the periphery of the wafer) fall before the end of the process. The consequence is that the microneedles underneath are no longer protected and as a consequence no longer etched in a controlled manner. Problems therefore arise, in particular microneedle malformation and low production yields.

GENERAL DESCRIPTION OF THE INVENTION

The problems discussed in the previous chapter are eliminated or at least notably reduced with the microneedle manufacturing process according to the invention which is characterized by the creation of bridges which link the hats between each others as well as between hats and edges during the manufacturing process.

More exactly the invention concerns an out-of-plane microneedle manufacturing process comprising the simultaneous creation of a network of microneedles and the creation of a polygonal shaped hat above each microneedle under formation, the process comprising the following steps:
   providing bridges between the hats,
   maintaining the bridges during the remaining microneedle manufacturing steps,
   removing the bridges, together with the hats, when the microneedles are formed.

In the present text, the expression "polygonal hat" has to be understood" as a closed figure consisting of straight lines joined end to end.

A "polygonal hat" in the sense of the present text also include a circle. This object may be viewed as a polygone with straight lines tending towards zero.

Like the hats, the bridges are totally removed at the end of the manufacturing process and result in no modification of the microneedle design.

The bridges are preferably made of suspended structures.

They have a design which is compatible with the materials of the suspended structures and the microneedle fabrication process.

The bridges may have many different designs.

In one embodiment they are rectilinear.

In another embodiment they comprise a curved portion.

Advantageously, each bridge consists of a combination of rectilinear segments and of circle portions, e.g. of ½ and ¼ circles.

The bridge dimensions can vary depending on the distance between the microneedles as well as the distance between the microneedles and the edge of the wafer. The thickness of the bridges which is linked to the thickness of the hats can vary between 100 nm and 100 um: The width of the bridges can vary between 1 um and 100 um.

Moreover certain physical properties such as the mechanical resistance are affected by the size and shape of the bridges.

The material used must have the appropriate characteristics to support the manufacturing process. For example, for a process requiring an excellent conductivity, metal would be chosen.

Multilayered bridges, in particular with three layers, offer an interesting compromise when different properties are required as for example good conductivity, high selectivity and mechanical resistance to deformation.

DETAILED DESCRIPTION OF THE INVENTION

The invention is discussed below in a more detailed way with examples illustrated by the following figures.

NUMERICAL REFERENCES USED IN THE FIGURES

Figure 1:
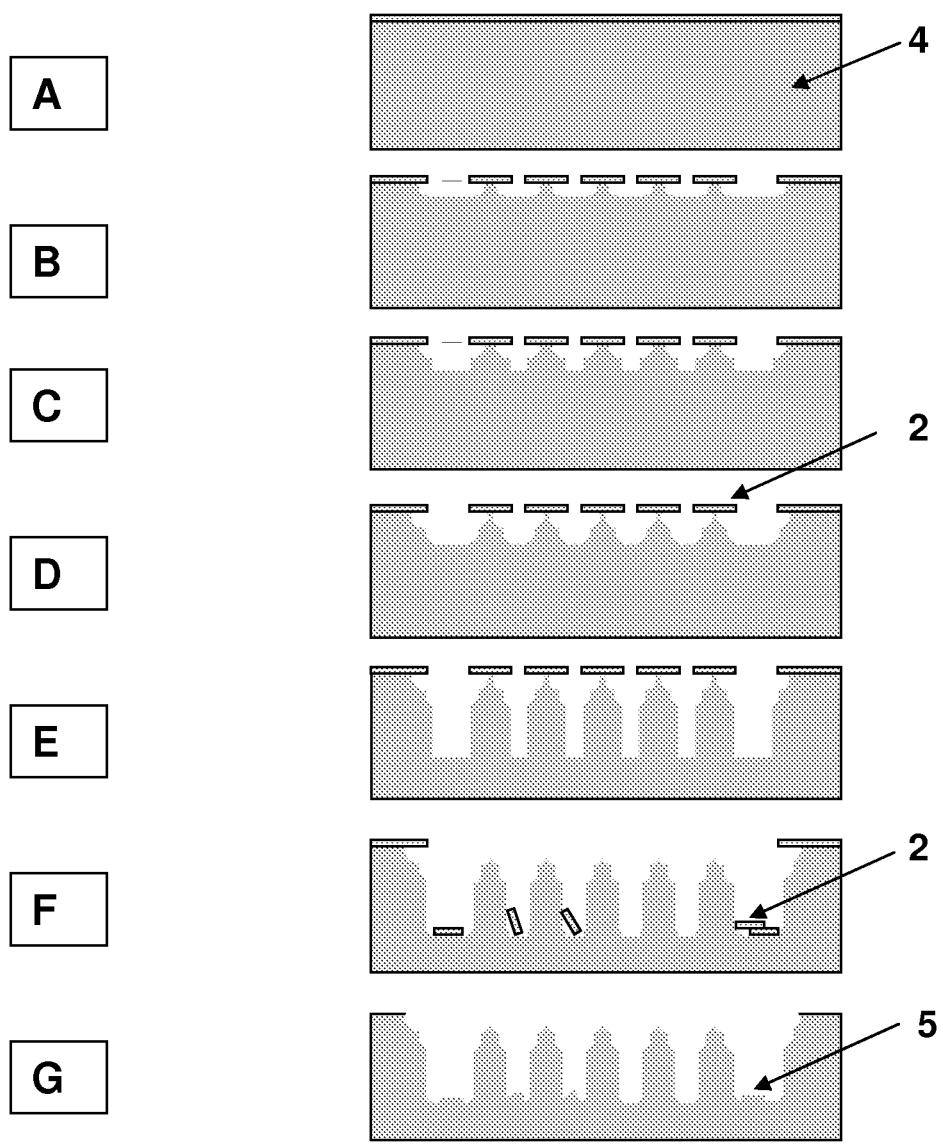
FIG. 1 shows a microneedle manufacturing process according to the state of the art.

1. Microneedle
2. Hat
3. Bridge

4. Wafer
5. Damaged area
6. Rectilinear segment
7. ½ circle
8. ¼ circle
9. Metal layer
10. SiO₂ layer State of the art MEMS microneedle fabrication process as described in FIG. 1 usually starts with a wafer, preferably a silicon wafer 4. On top of this silicon wafer a silicon dioxide layer is used as a protective mask to pattern the microneedles.

Figure 4:
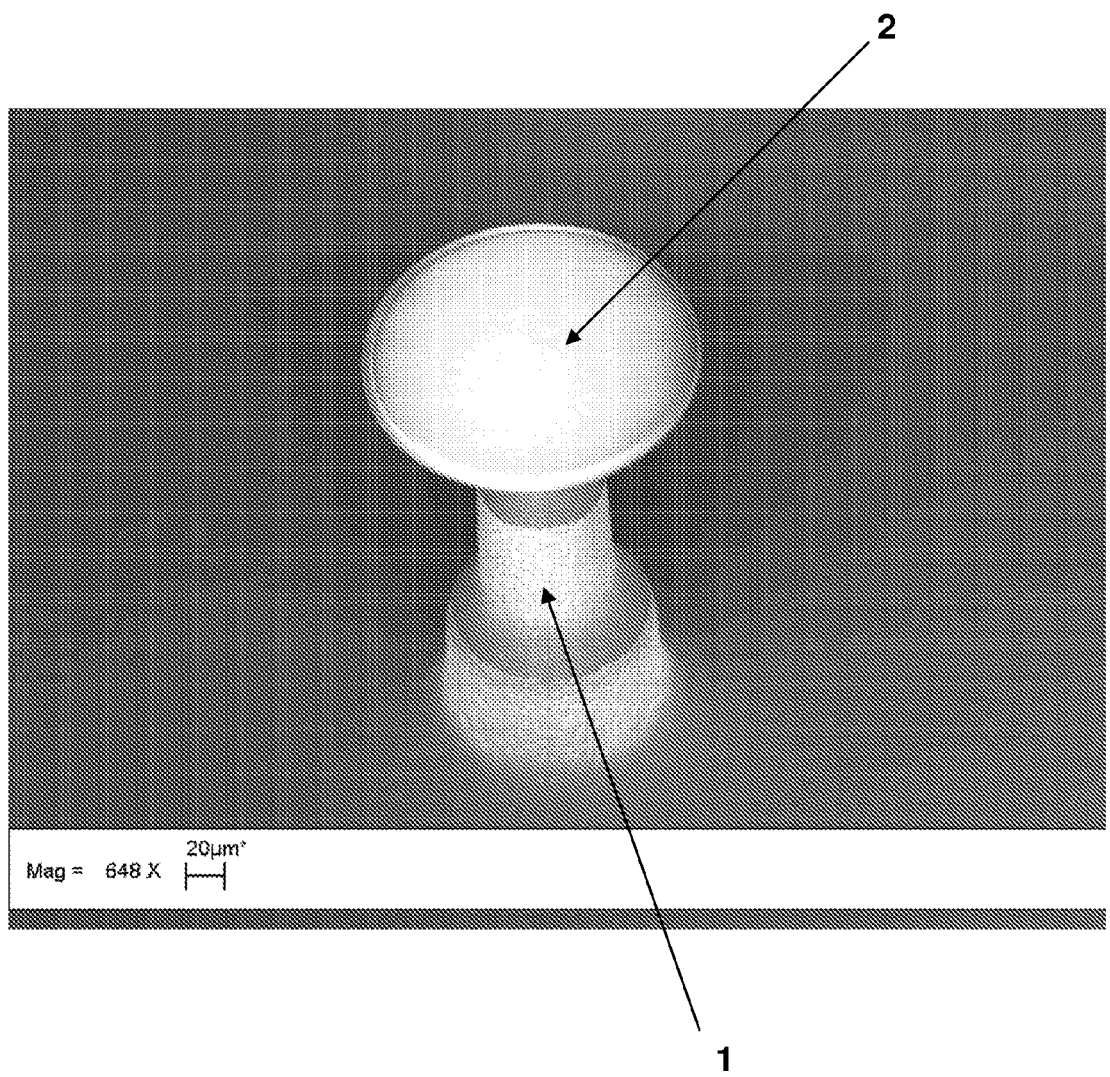
FIG. 4 is a picture of an assembly microneedle-hat according to the state of the art (without bridges)

This process aims at obtaining microneedles separated from each others and as a consequence the continuous protective mask in step A becomes discontinue at the start of the structuration of the microneedles step B. The parts of this discontinuous protective mask are called hats 2 and each microneedle is overlooked by a hat, protecting the microneedle and allowing controlled and well defined structuration. FIG. 4 shows an example of a microneedle creation 1 under a hat 2.

This structuration of the microneedles is performed by a sequence of isotropic and anisotropic etches as represented in FIG. 1 steps B to E.

The first isotropic etch as represented in FIG. 1 step B initiates the tip of the microneedle. The first anisotropic etch (FIG. 1, step C) is used to define the head of the microneedle.

The goal of the second isotropic etch as represented in FIG. 1 step D is to initiate the shoulder of the microneedle and to separate the head of the microneedle with the shaft which is obtain thanks to the second anisotropic etch (FIG. 1, step E). Finally comes the last isotropic etch (FIG. 1, step F) which is the most important etch of the process. Thanks to this etch, we pattern the tip of the microneedle, the backside trough holes and the final design of the microneedle.

An oxidation and a silicon oxide etch as represented in FIG. 1, step G are then realized to remove the hats and to polish the silicon surface.

Frequently hats may fall before the end of the process (FIG. 1, step F, Ref. 2): This leads to a situation in which the structuration of the microneedle becomes uncontrolled resulting in malformation and low production yields. In addition the fallen hats provoke a bad surface state as shown in FIG. 1 Ref 5.

Figure 2:
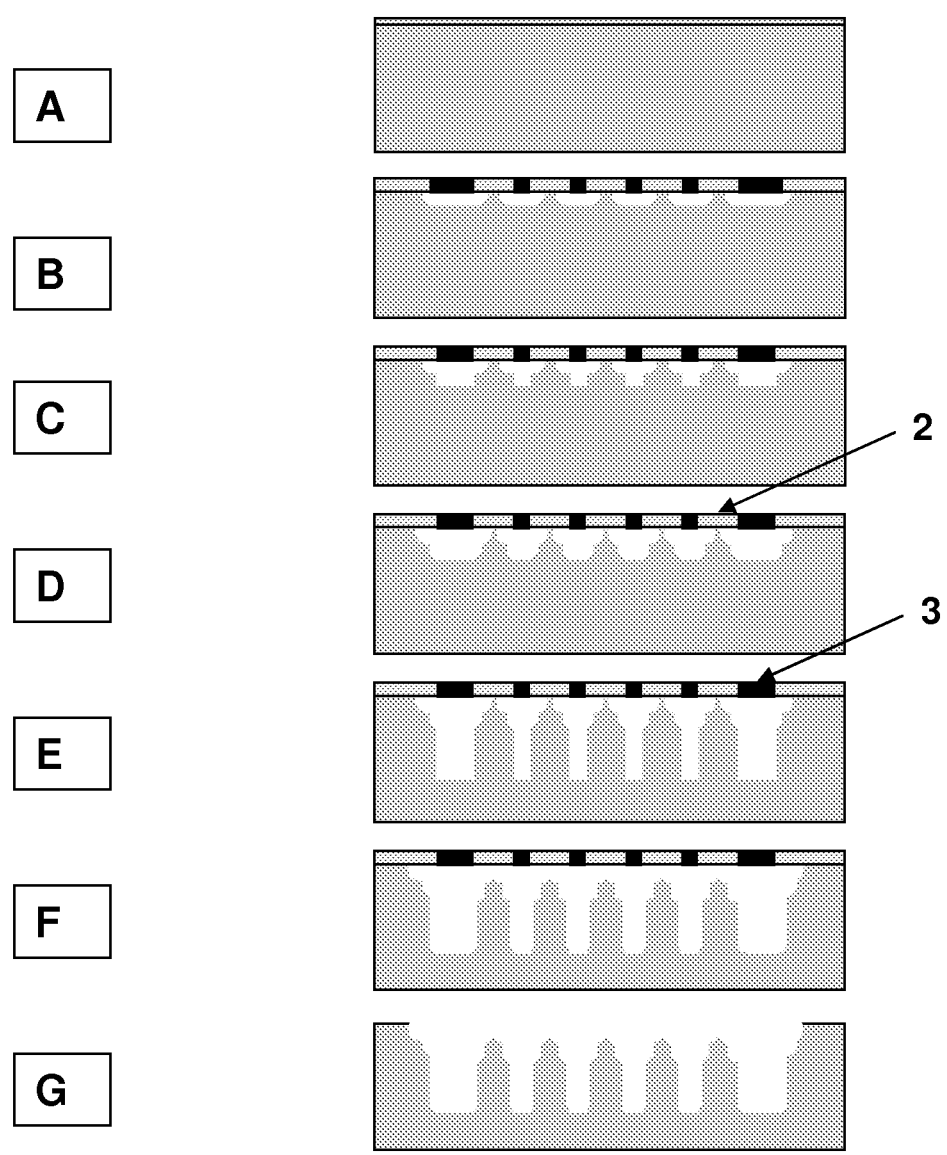
FIG. 2 shows a microneedle manufacturing process according to the invention.
Figure 3:
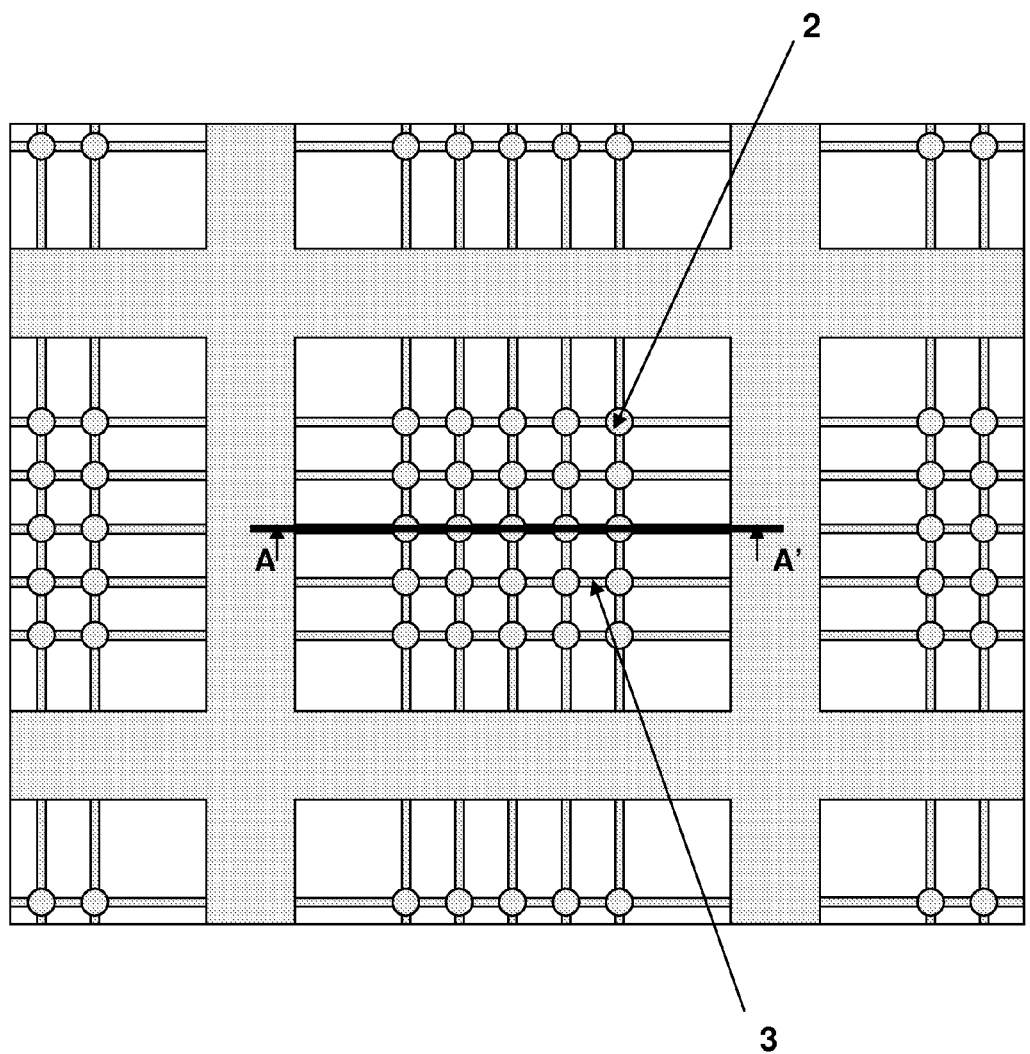
FIG. 3 is an upper view of the element shown in FIG. 2.
Figure 11:
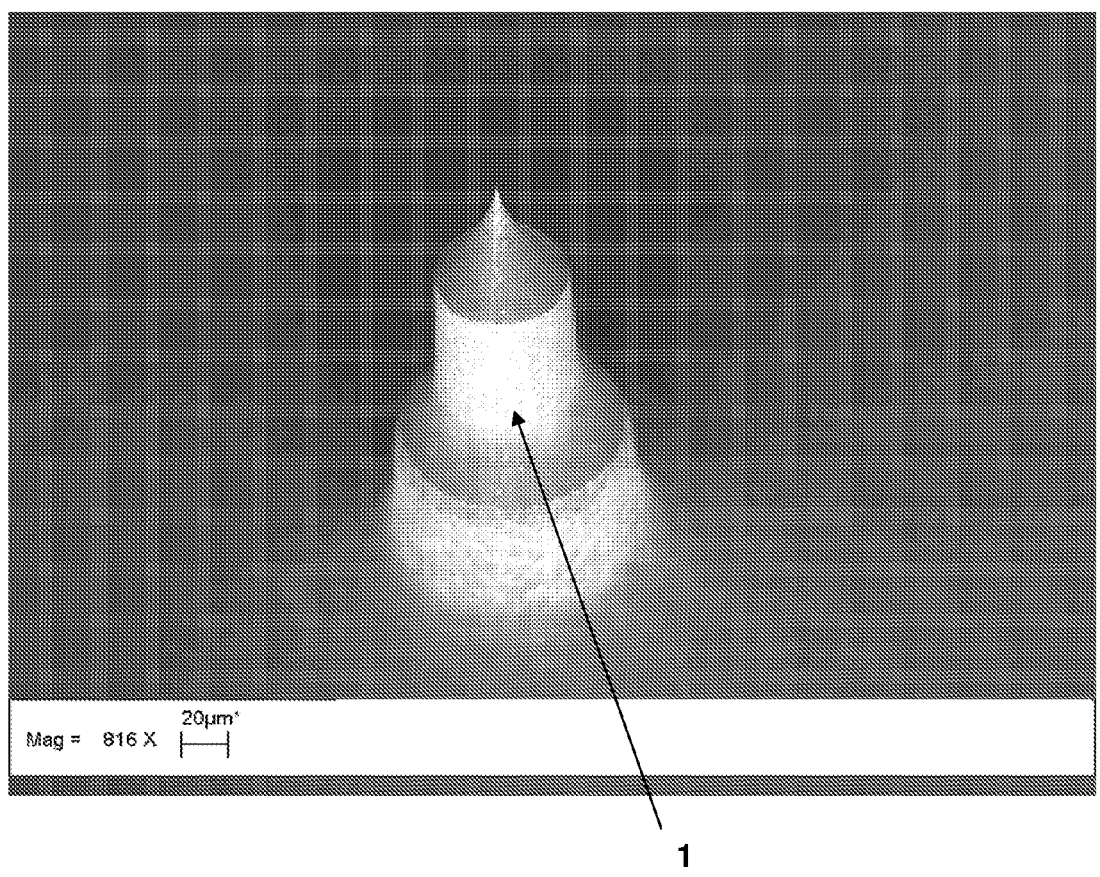
FIG. 11 is a picture of a microneedle obtained with a process according to the invention.

The present invention provides a way to hold the hats together so that they won't fall before the end of the process. To this effect the hats are linked together and are linked to the edges as displayed in FIG. 3. These links (FIG. 2, Ref 3), also named bridges in the present text, will stay in place up to the end of the process and guarantee the stability of each hat until the microneedle fabrication is ended (FIG. 2 Step F). When the process has been completed (FIG. 1 step G) the hat and their links are removed revealing perfect microneedles pattern (see e.g. FIG. 11) and chip surface state.

An important advantage of these links is that they do not modify the microneedle structuration parameters. The isotropic and anisotropic etches are the same with or without links.

As described earlier bridges and hats are deeply linked together; as a matter of fact their are made of same materials and have the same thickness.

Figure 5:
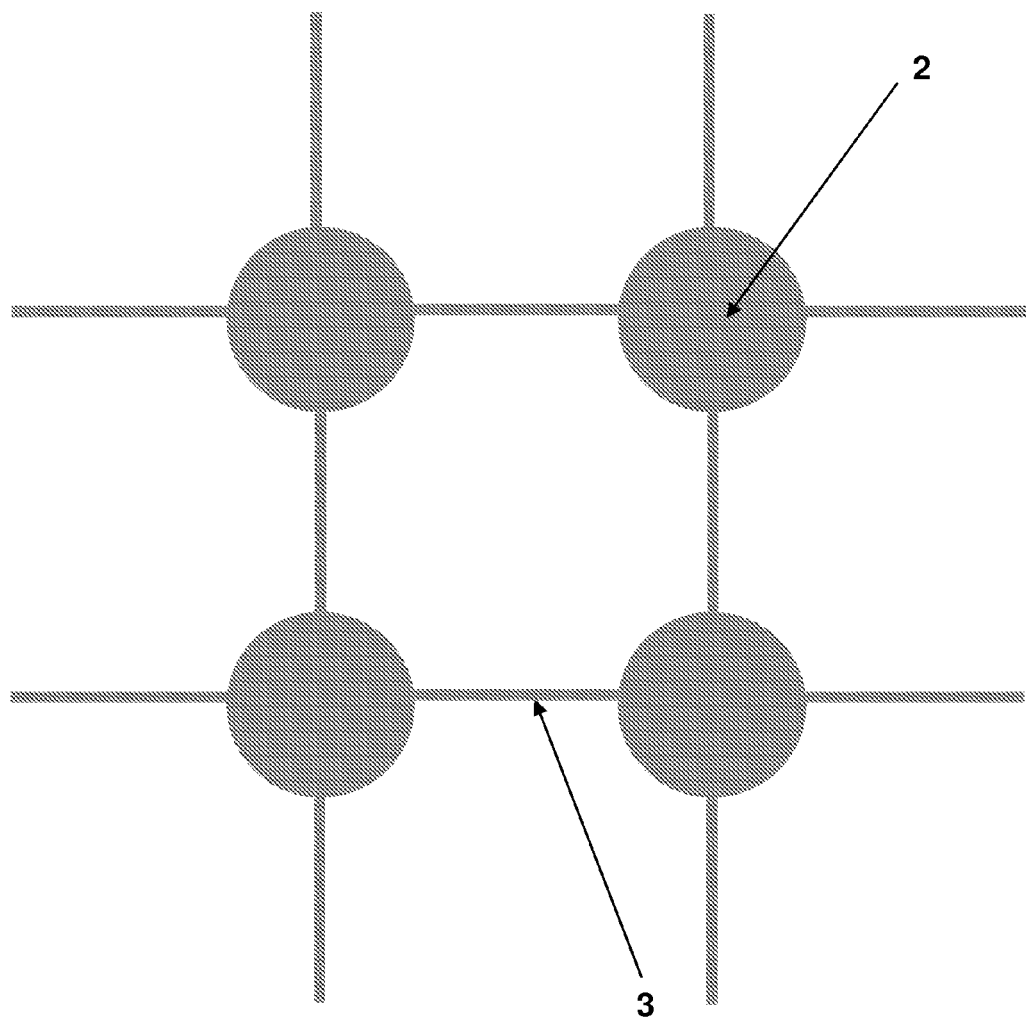
FIG. 5 shows one example of bridges according to the invention.
Figure 9:
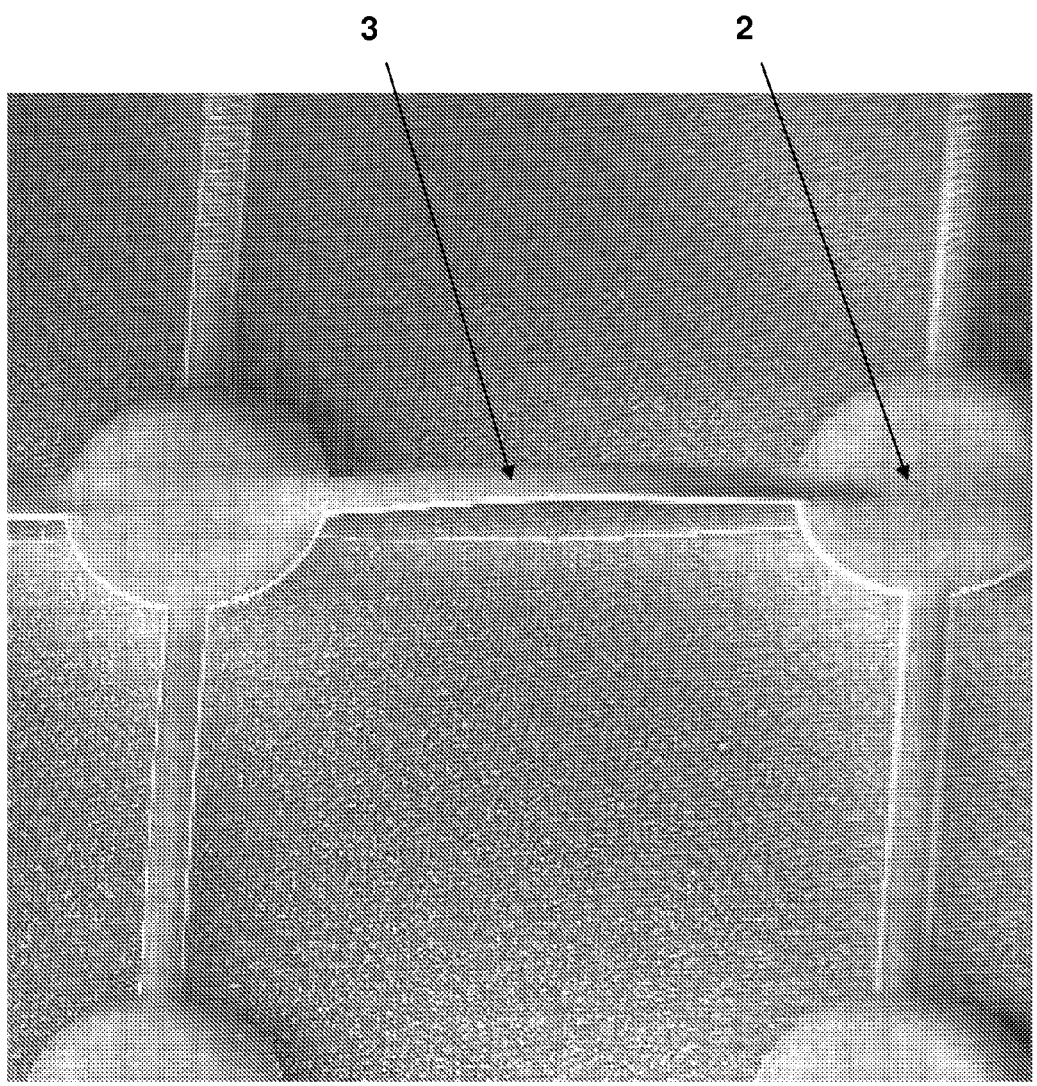
FIG. 9 is a picture of the example shown on FIG. 5.

As far as the design of the bridges is concerned it can take many forms. Simple linear bridge between the hats can be an option as shown schematically in FIG. 5 and on the picture in FIG. 9 which represents microneedle process of step B in FIG. 1.

Figure 6:
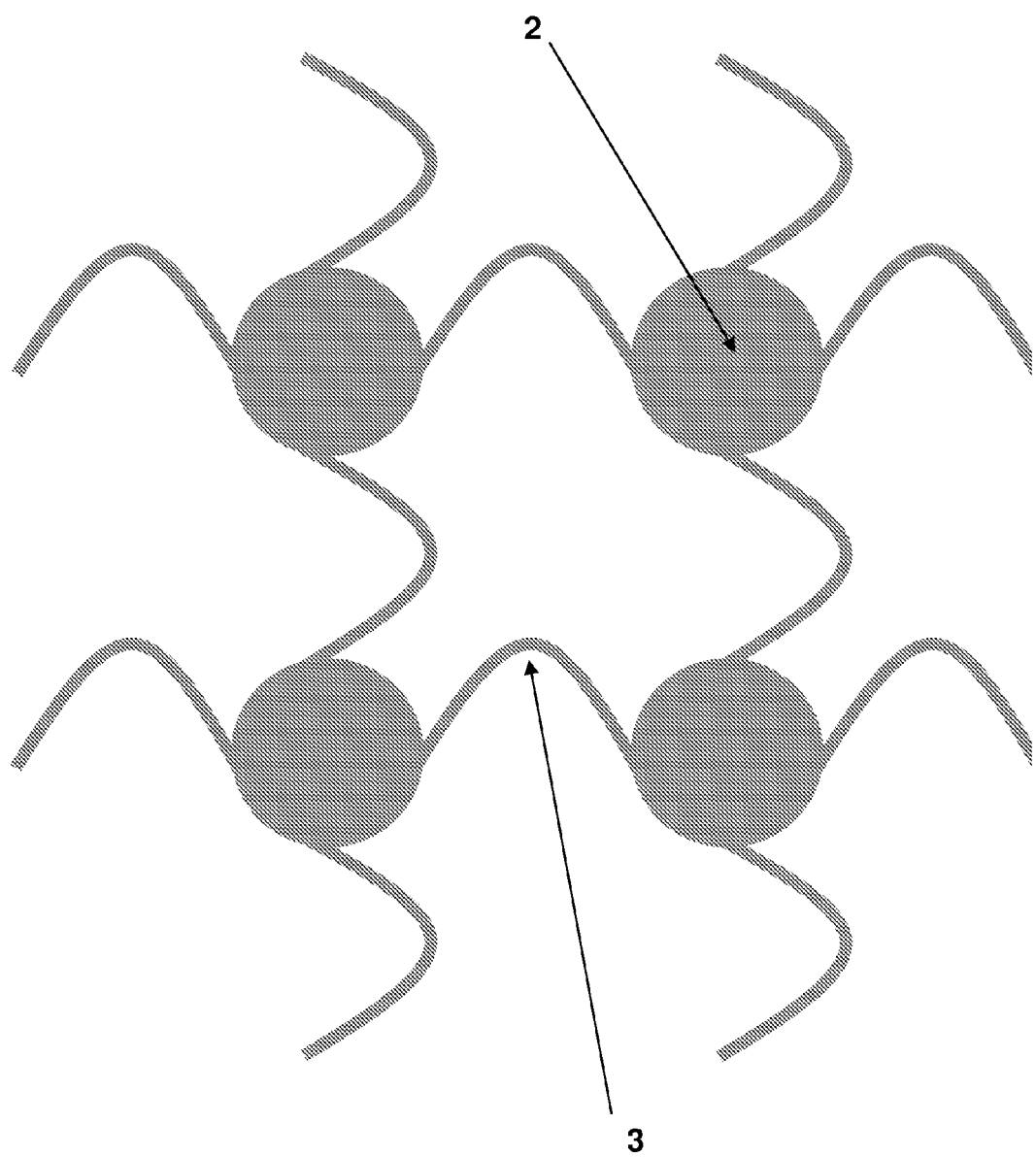
FIG. 6 shows another example of bridges according to the invention.
Figure 7:
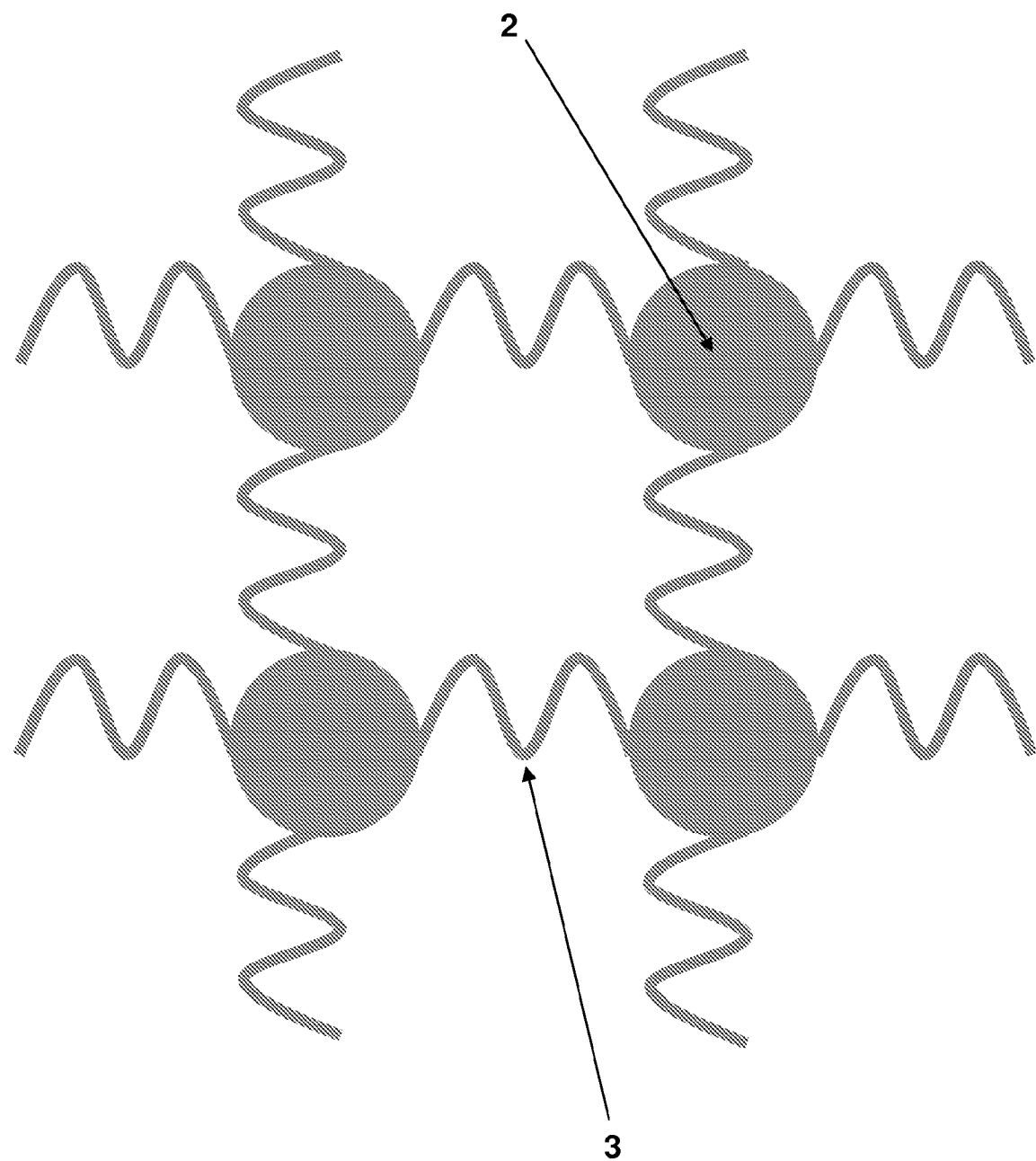
FIG. 7 shows another example of bridges according to the invention.
Figure 8:
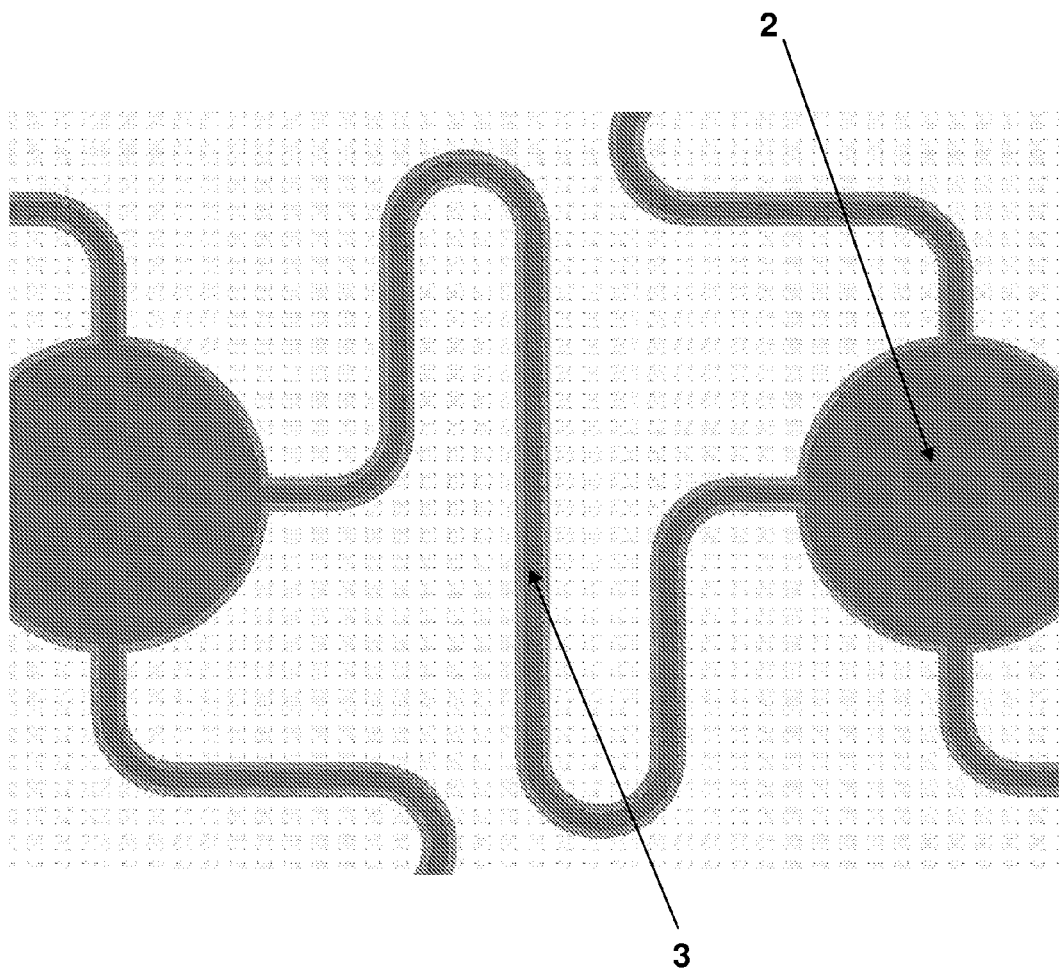
FIG. 8 shows another example of a bridges according to the invention.

Curved segments as in FIG. 6 and FIG. 7 or combination of rectilinear and curved segments as in FIG. 8 are also possible.

Figure 10:
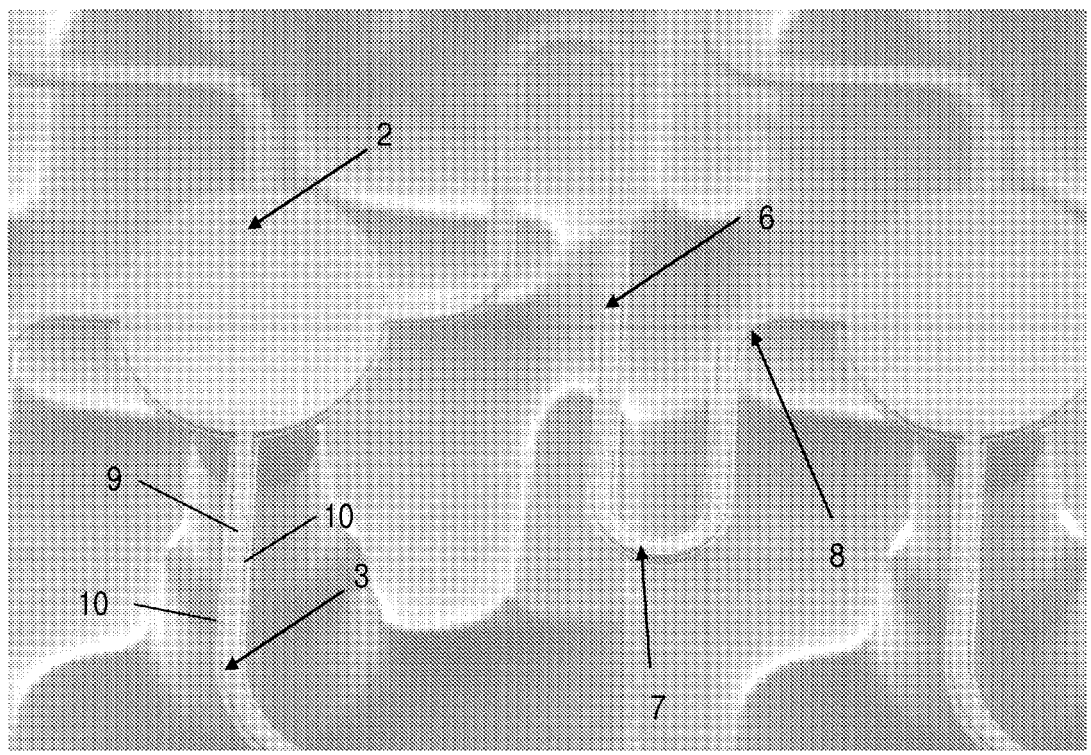
FIG. 10 is a picture of microneedles with hats and bridges before removal (status before FIG. 11)

Another aspect of the design of the bridges is the material. Single layer bridges can be appropriate for many processes but depending on the complexity of the process and also on the cleaning steps multilayer bridges can be a better option. Multilayered bridges improve the characteristics of the bridges (FIG. 10). We may associate metal layers (aluminium, tungsten, nickel . . . ) and no conductive layers (silicon dioxide, silicon nitride . . . ). The metal layers improve the thermal conductivity of the bridges and the non conductive layers improve the mechanical resistance and the high selectivity of the bridges.

The invention claimed is:

1. An out-of-plane microneedle manufacturing process comprising:
    providing a wafer on which a silicon dioxide layer is used as a protective mask to pattern a microneedle,
    said process further comprising the following successive steps that etch the wafer in order to structure the microneedle:
        initiating a tip of the microneedle by using a first isotropic etch,
        defining a head of the microneedle by using a first anisotropic etch,
        initiating a shoulder of the microneedle by using a second isotropic etch,
        obtaining a shaft of the microneedle by using a second anisotropic etch,
        patterning the tip of the microneedle and a final design of the microneedle by using a third isotropic etch;
    wherein the tip of the microneedle is patterned only by the third isotropic etch.

2. An out-of-plane microneedle manufacturing process comprising:
    providing a wafer on which a silicon dioxide layer is used as a protective mask to pattern a microneedle,
    said process further comprising the following successive steps that etch the wafer in order to structure the microneedle:
        using a first isotropic etch that etches a tip of the microneedle,
        using a first anisotropic etch that etches a head of the microneedle,
        using a second isotropic etch that etches a shoulder of the microneedle,
        using a second anistropic etch that etches a shaft of the microneedle,
        using a third isotropic etch that patterns the tip of the microneedle and a final design of the microneedle.

3. An out-of-plane microneedle manufacturing process comprising:
    providing a wafer,
    forming a protective mask on the wafer, said protective mask comprising at least one hat to pattern at least one microneedle and at least one bridge to insure the stability of said at least one hat,
    said process further comprising the following successive steps that etch the wafer in order to structure the microneedle:
        initiating a tip of the microneedle by using a first isotropic etch,
        defining a head of the microneedle by using a first anisotropic etch,
        initiating a shoulder of the microneedle by using a second isotropic etch,
        obtaining a shaft of the microneedle by using a second anisotropic etch, patterning the tip of the microneedle and a final design of the microneedle by using a third isotropic etch,
wherein the tip of the microneedle is patterned only by the third isotropic etch.

4. The process according to claim 3 further comprising:
removing the protective mask.

\* \* \* \* \*

UNITED STATES PATENT AND TRADEMARK OFFICE
CERTIFICATE OF CORRECTION

PATENT NO. : 8,999,177 B2
APPLICATION NO. : 12/808334
DATED : April 7, 2015
INVENTOR(S) : Cachemaille et al.

It is certified that error appears in the above-identified patent and that said Letters Patent is hereby corrected as shown below:

IN THE CLAIMS

Column 4, line 18, change "comprising" to —consisting essentially of—;

Column 4, lines 31-32, change "wherein the tip of the microneedle is patterned only by the third isotropic etch" to —wherein no sidewall mask is used in any etching step—;

Column 4, line 37, change "comprising" to —consisting essentially of—;

Column 4, line 49, change "microneedle." to
—microneedle;

wherein no sidewall mask is used in any etching step.—;

Column 4, line 57, change "comprising" to —consisting essentially of—;

Column 5, lines 3-4, change "wherein the tip of the microneedle is patterned only by the third isotropic etch." to —wherein no sidewall mask is used in any etching step.—.

Signed and Sealed this
Twenty-third Day of February, 2016

Michelle K. Lee
*Director of the United States Patent and Trademark Office*